United States Patent [19]

Carra et al.

[11] 4,368,347
[45] Jan. 11, 1983

[54] PROCESS FOR THE SEPARATION OF METAXYLENE FROM MIXTURES OF AROMATIC HYDROCARBONS

[75] Inventors: Sergio Carra; Elio Santacesaria; Massimo Morbidelli; Franco Codignola; Lucio DiFiore, all of Milan, Italy

[73] Assignee: Sisas S.p.A., Milan, Italy

[21] Appl. No.: 214,286

[22] Filed: Dec. 8, 1980

[30] Foreign Application Priority Data

Aug. 7, 1980 [IT] Italy ............................... 24044 A/80

[51] Int. Cl.³ ........................... C07C 7/12; C07C 7/14
[52] U.S. Cl. .................................... 585/828; 585/826; 585/820; 208/310 Z
[58] Field of Search .................... 585/828, 820, 826; 208/310 Z

[56] References Cited

U.S. PATENT DOCUMENTS

| | | | |
|---|---|---|---|
| 2,988,502 | 6/1961 | Ricards et al. | 208/310 Z |
| 3,053,913 | 9/1962 | Norris | 208/310 Z |
| 3,114,782 | 12/1963 | Fleck et al. | 585/831 |
| 3,126,425 | 3/1964 | Eberty, Jr. et al. | 585/828 |
| 3,558,730 | 1/1971 | Neuzil et al. | 585/828 |
| 3,558,732 | 1/1971 | Neuzil et al. | 585/828 |
| 3,686,342 | 8/1972 | Neuzil | 505/828 |
| 3,700,744 | 10/1972 | Bereju et al. | 585/828 |
| 3,773,846 | 8/1972 | Bereju et al. | 585/828 |
| 3,795,711 | 3/1974 | Worrell et al. | 208/310 Z |

FOREIGN PATENT DOCUMENTS

| | | | |
|---|---|---|---|
| 49-43939 | 11/1974 | Japan | 585/828 |
| 898058 | 6/1962 | United Kingdom | 208/310 Z |

*Primary Examiner*—Delbert E. Gantz
*Assistant Examiner*—Helane E. Maull
*Attorney, Agent, or Firm*—Cushman, Darby & Cushman

[57] ABSTRACT

A process for the separation of metaxylene from aromatic $C_8$ hydrocarbons, particularly from ethylbenzene and paraxylene, wherein a first phase is provided in which the mixture of aromatic hydrocarbons is selectively adsorbed, in vapor phase, into a catalytic bed consisting of zeolite of the Y type, preliminarily exchanged with potassium, and in a second phase a desorption is effected with a suitable solvent. The process, carried out at a temperature of 150° to 200° C. and preferably at atmospherical pressure, permits the recovery of metaxylene, substantially pure and at a concentration much higher than that of the starting mixture.

11 Claims, 6 Drawing Figures

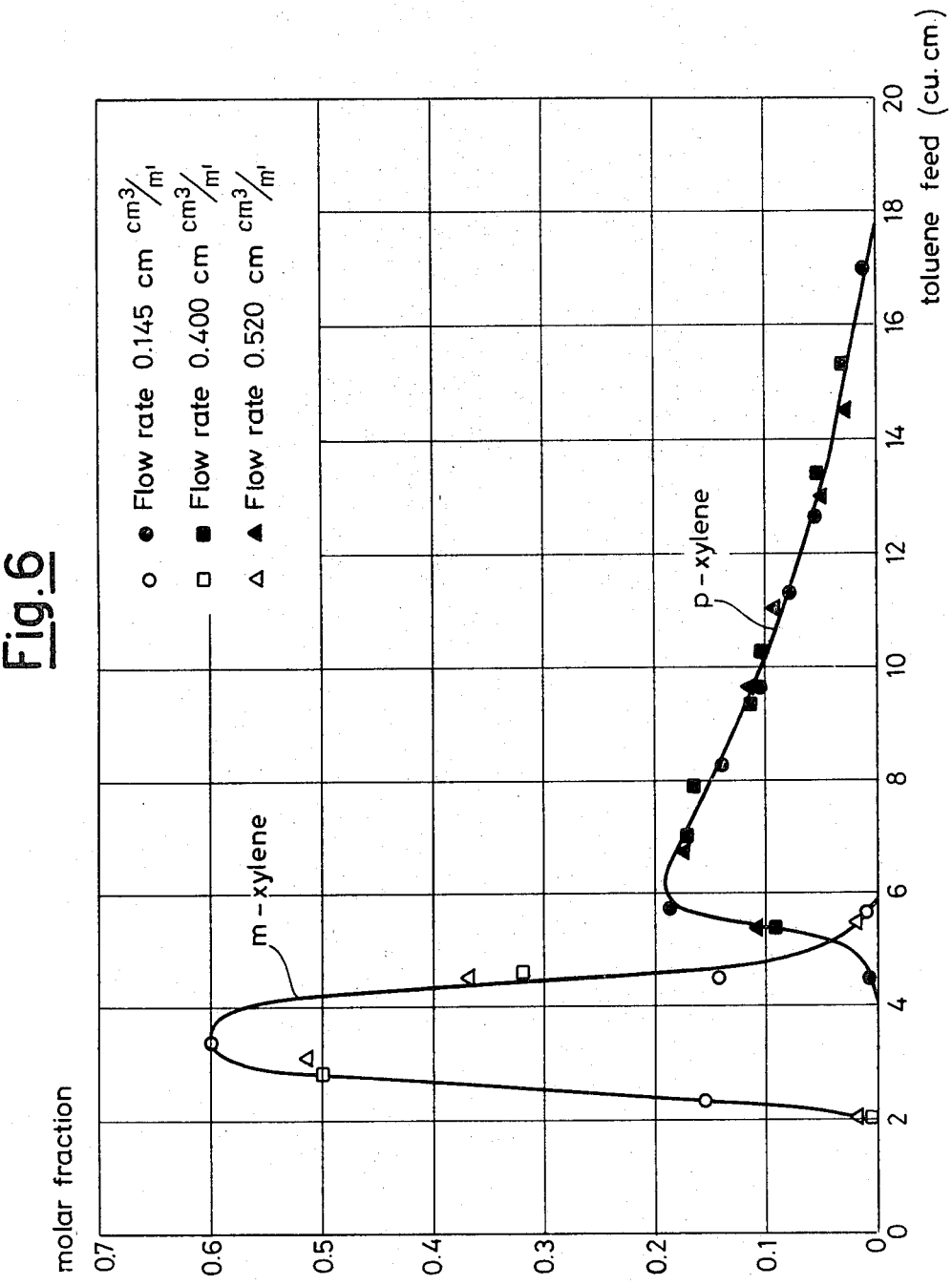

PROCESS FOR THE SEPARATION OF METAXYLENE FROM MIXTURES OF AROMATIC HYDROCARBONS

The present invention relates to a process for the separation of metaxylene from mixtures of aromatic hydrocarbons and, more specifically, for the obtaining of metaxylene at high degree purity from mixtures of $C_8$ aromatic hydrocarbons.

BACKGROUND OF THE INVENTION

Metaxylene has recently found use in the production of isophtalic acid, whereby it is industrially interesting to be able to have this raw material available at a high purity degree and at low cost.

Metaxylene and orthoxylene, which cannot be separated by adsorption on the tested zeolitic material, require the separation by distillation of the orthoxylene, to be indifferently carried out either before or after the adsorption process. In the following, thus, when speaking about adsorption, orthoxylene shall not be considered, it being meant that it follows the pattern of the metaxylene, unless it has already been separated by preliminary distillation.

It is known that in the case of isomer aromatic hydrocarbons of the $C_8$ type, the separation of the constituent single hydrocarbons is a difficult operation due to the proximity of the boiling points and to the resemblance of the other chemical and physical properties of these hydrocarbons.

According to the traditional techniques, in fact, orthoxylene was separated by distillation, since it has a boiling point 5.3° C. higher than metaxylene. Ethylbenzene was separable, with much greater difficulty, always by distillation, in superfractionation columns of more than 300 trays. The paraxylene, on the contrary, was purificable from metaxylene, by fractionated crystallization. Such a process, however, was affected by a number of problems, owing to the forming of an eutetic mixture with metaxylene.

More recently, the separation of paraxylene or of ethylbenzene has been effected by selective adsorption on materials of the zeolitic type. A number of patents evidence the relevant activity in this field. The zeolitic materials proposed for separation are the most dissimilar: anyhow, in most of the cases sodium zeolites of the X or Y types are used, i.e. of the type having large pores, exchanged with ions such as: potassium, barium, cesium, rare earths, mixed, etc. The separation is always carried out in liquid phase by dividing the process into two steps: adsorption and desorption.

In the desorption phase another component is introduced which, having a substantial affinity for the solid, facilitates the operation. The desorption phase, being usually the slower one, does condition the process. Consequently, the selection of the desorbent and of the desorption conditions is essential for the good success of the process, because the desorbent must be recovered by distillation. Thus one will use a desorbent that is easily separable by distillation and above all the amount to be used is to be kept at minimum, also for a better exploitation of the adsorption bed. In the liquid phase such a result has been achieved in a process for the recovery of paraxylene according to which the positions of drawing and feeding are intermittently displaced along the adsorption bed.

As the desorbent there have been used, for instance, benzene, toluene, diethylbenzenes, ethers, alcohols, dienes, ketones, etc.

All the processes developed to date, have as their purpose producing pure paraxylene or ethylbenzene. Instead the separation of metaxylene has been industrially carried out up to date only by selective solfonation or by extraction with $HF.BF_3$. These processes have substantial drawbacks due to the corrosion effects.

In U.S. Pat. No. 3,773,846 to Berger the use of zeolitic materials is claimed for simultaneous production of paraxylene and metaxylene having a high purity.

In fact, according to this process, paraxylene is separated by adsorption.

The fraction of xylenes impoverished of paraxylene, which is simultaneously obtained, undergoes a complicated series of operations of traditional type comprising: fractionated crystallization, distillation and isomerization, in order to obtain metaxylene with a high degree of purity.

In the U.S. Pat. No. 3,114,782 another process is proposed for the separation of aromatic hydrocarbons from mixtures, the process being indifferently workable in the liquid or in the vapor phase and in which, thanks to the use of a partially dehydrated zeolite X, during the flow of the mixture of $C_8$ aromatic hydrocarbons, the metaxylene is selectively adsorbed whereas the effluent is enriched with paraxylene and with the other components scarcely adsorbed. It is important to point out that in the process described in this patent the operating conditions, namely to carry out the operation in liquid and in vapor phase, are considered wholly equivalent and thus without influence.

In the case also of the U.S. Pat. No. 3,126,425 selective adsorption in vapor phase of a xylene mixture onto a zeolite of the X type, preferably exchanged with calcium, is carried out. Orthoxylene and metaxylene are preferentially retained in the zeolite, leaving an unadsorbed effluent enriched with paraxylene, namely with the desired product.

Consequently, on the basis of the information known from the prior art it was foreseen:
 (a) to carry out the adsorption in liquid phase, with a zeolite of the X or Y type, with selective adsorption of paraxylene;
 (b) to carry out the adsorption in vapor phase with a zeolite of the type X with large pores, the metaxylene being preferably retained (together with orthoxylene).

Not negligible considerations and theoretical problems are to be added thereto.

As regards the adsorption in the vapor phase, in fact, it must be observed that owing to the very short times of permanence or contact with the particles of the adsorbent, one would be disposed to exclude, from the conceptual point of view, that separation between the xylenes can take place at a substantial rate.

For these and other reasons, in fact, an adsorption technique for the direct separation, in vapor phase with high yields and concentrations, of metaxylene from mixtures of $C_8$ isomers has never been used. The main purpose of the present invention is that of providing an industrial process which permits metaxylene to be separated from mixtures of aromatic $C_8$ hydrocarbons.

A more specific purpose of the invention is that of providing an industrial process by which there is particularly obtained high purity metaxylene and further is eventually possible to recover other aromatic $C_8$ hydrocarbons, with a high degree of purity as well.

DETAILED DESCRIPTION OF THE INVENTION

Figure 1:
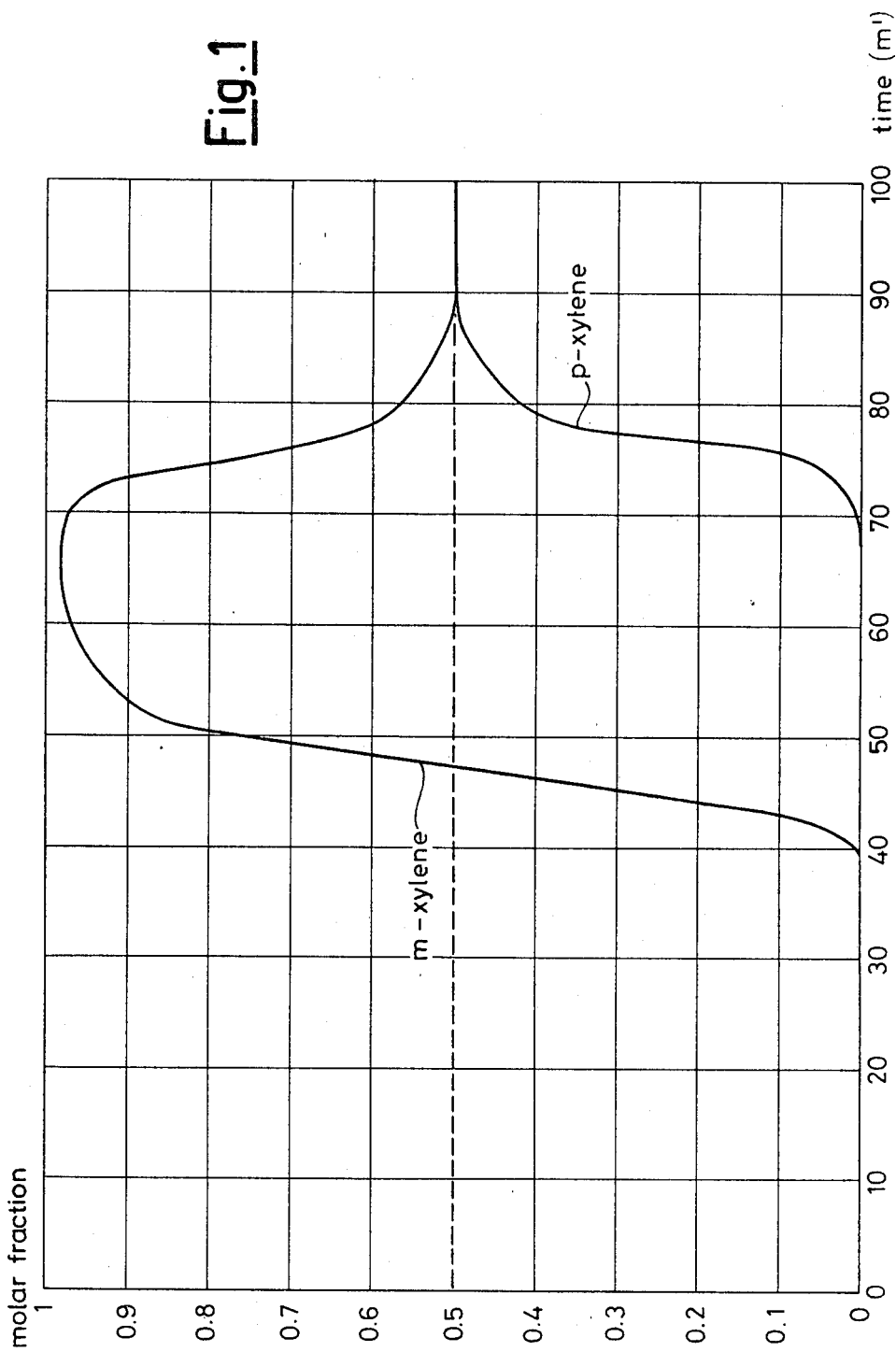

These and other purposes are achieved by a process for the separation of metaxylene from aromatic $C_8$ hydrocarbons, by adsorption on zeolitic materials and subsequent desorption with a solvent, characterized in that the operation is carried out in vapor phase, with a zeolite having large pores, of the type Y, preliminarily exchanged at the maximum possible rate with potassium ions, at a temperature of between 145° C. and 250° C. and at a pressure comprised between the atmospheric pressure and 2 atmospheres, the adsorption bed being already saturated with the desorbent and the process being carried out so as to collect the metaxylene which, due to its low affinity for the solid, has a migration rate along the column greater than the other components of the mixture and comes out first with high concentration and purity.

The present invention consequently consists in the separation of metaxylene from aromatic $C_8$ hydrocarbons, by adsorption from the vapor phase on zeolitic materials having large pores and of the Y type, preliminarily exchanged as much as possible with potassium.

The exchange is carried out by feeding onto a bed of zeolitic material, in form of extruded pellets of 1.58 mm diameter and 3 mm average length, a 7% by weight aqueous solution of KCl, at a temperature of between 80° and 100° C., until by analysis no traces of the exchanged ion are found which were not already contained in the feed. For a complete exchange between sodium and potassium there are needed contact times between the solid and the solution of at least 2 hours, preferably 5 or 6 hours are required. The zeolite exchanges 98% or more of the sodium initially present. The zeolite is washed with warm distilled water, dried at 100° C. for 3 hours and then treated at 400°–600° C. for 2–4 hours for the complete dehydration.

The thus prepared zeolite has a remarkable affinity towards the paraxylene. Such an affinity is lower for ethylbenzene and still lower for meta and orthoxylene. The latter isomers show, among other things, a reciprocal separation factor near to unity. For this reason they can be separated from each other only by having recourse as already mentioned to other means such as for instance distillation.

The operating conditions employed are the following: temperature between 145° C. and 250° C., preferably between 150° and 200° C., and pressure between the atmospherical pressure and 2 atm., preferably atmospherical pressure.

The loading capacity for the described zeolites is 0.13–0.17 g of adsorbed xylenes per gram of zeolite.

The present invention is based on three fundamental features, of which the first relates to the possibility of directly separating the metaxylene, as the first product coming out, by passing a certain amount of mixture of aromatic $C_8$ hydrocarbons, in vapor phase, in a column of the above described adsorbent.

The amount of xylene mixture to be fed onto the zeolitic bed, for the whole adsorption phase, is consistent with the amount of zeolite present in the column and can be determined from the loading capacity of the adsorbent solid, under the adopted operating conditions, possibly supplemented with the amount necessary to push the separated metaxylene out of the adsorbent bed, or other fractions which would have to be recovered in this phase.

It is also possible to carry out the operation with lower amounts and it improves the separation between the components, with a corresponding increase of concentration of desorbent in the single fractions collected.

The use of amounts of xylene mixture lower than that necessary in order to have the occurrence of the "break through" and the separation of metaxylene, has furthermore great importance in order to forecast the behaviour of the bed in the two phases of adsorption and desorption, as it will appear in example 5.

The second feature of the invention relates to the fact that the adsorption, as carried out under the described conditions, is neither to be considered a simple downing of the several components having greater affinity for the solid, nor it can be dealt with as an adsorption obeying to a linear isotherm. There occurs, on the contrary, a phenomenon which can only be compared with displacement chromatography whereby the adsorbed component, having greater affinity for the solid, acts in turn as the desorbent, enriching the top mixture with the component having the lesser affinity for the solid and coming out from the column at a concentration much higher than that in the feed. All this is the consequence of the fact that the xylenes fed into the bed are in competition for the adsorption, that the adsorption follows a law involving the saturation of the solid and that it is a perfectly reversible phenomenon.

Figure 2:
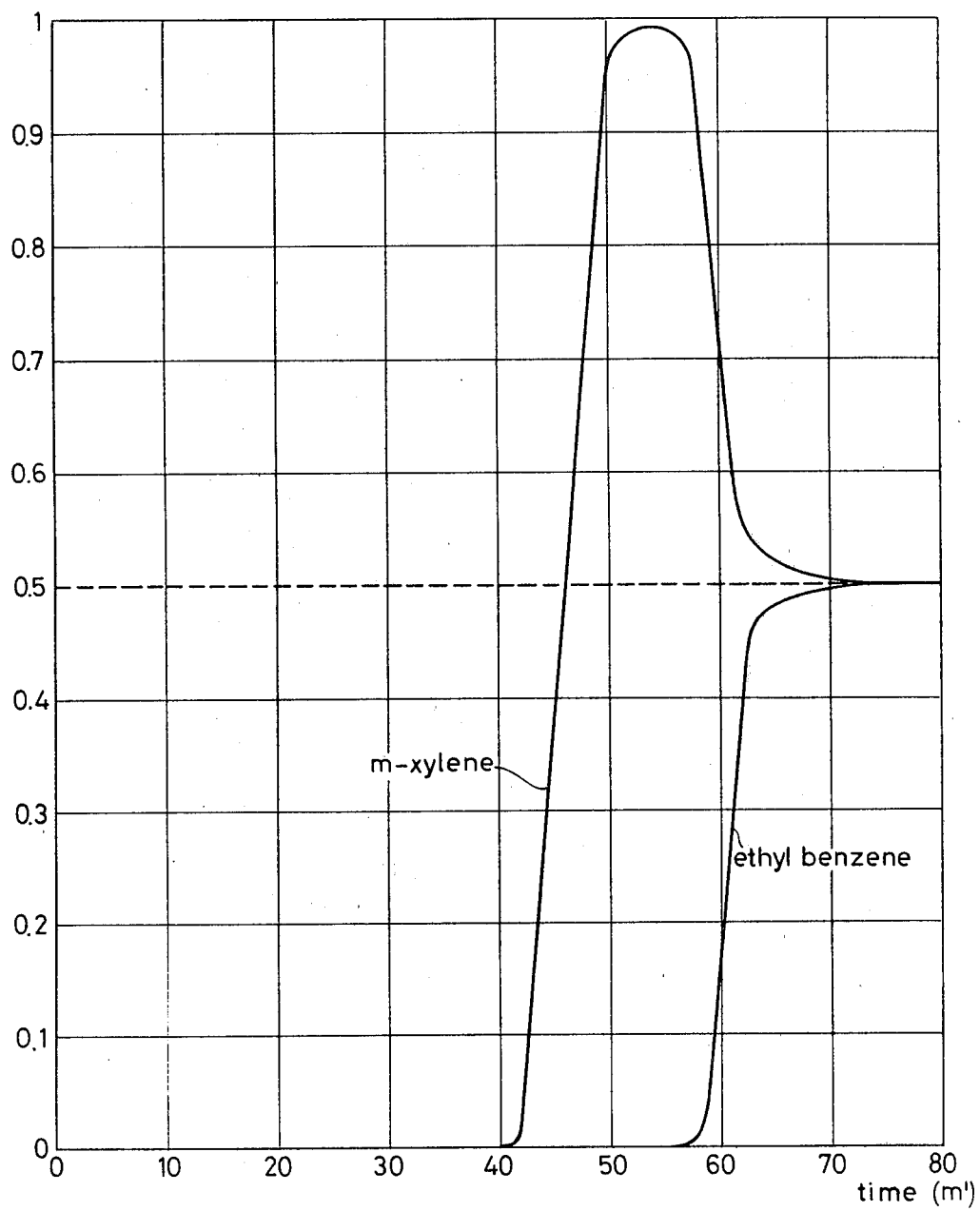
Figure 3:
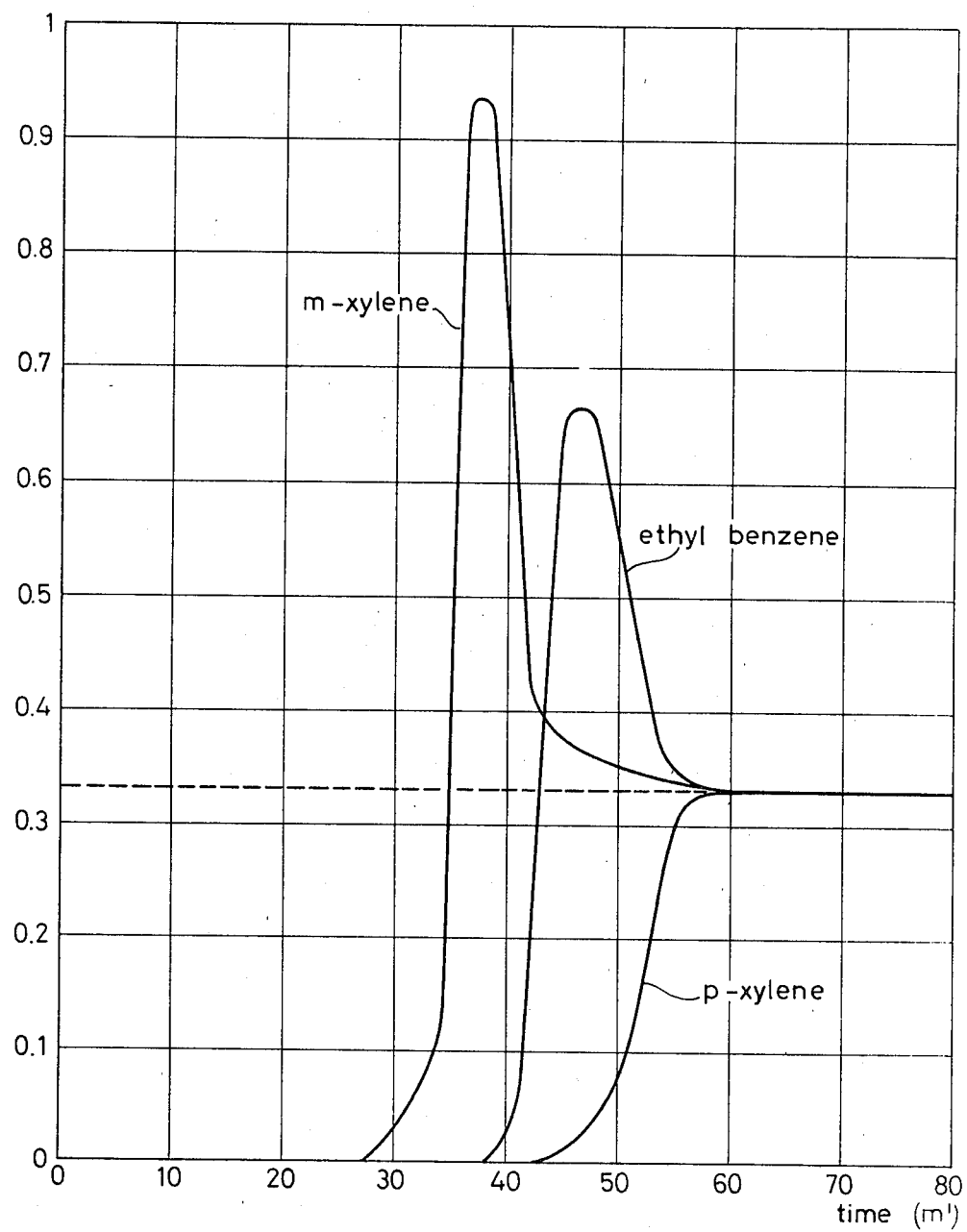

The described effect can be clearly seen in the break through curves as plotted in the FIGS. 1, 2 and 3, representing the molar fraction of the component appearing at the outlet of the column as a function of the passing time through the column or the adsorbent bed.

From the figures it is noted that the separated metaxylene achieves concentration rates near to 100%. From the break through curves of the above mentioned FIGS. 1 and 2 it is possible to determine the separation factor or selectivity $$\frac{C_1 q_2}{C_2 q_1}$$

$C_1$ and $C_2$ being the concentrations of the two components in the vapor phase and $q_1$ and $q_2$ the concentrations in the solid.

The selectivity values obtained for the several xylenes at 150° C. and at atmospherical pressure are reported in the following Table 1:

TABLE 1

Selectivity for the adsorption from vapor phase of xylenes onto zeolite exchanged with potassium.

| Component | Selectivity with respect to metaxylene |
|---|---|
| orthoxylene | 1 |
| araxylene | 4 |
| ethylbenzene | 1.9 |

The metaxylene enrichment, in the effluent vapor stream, which attains almost unitary molar fractions, would not be possible if the process is carried out in the liquid phase, since the sum of the void volume between the particles of the adsorbing solid and of the void volume between the particles of crystalline material forming the single pellets, is much higher than the intercrystalline zeolitic cavities, which only are responsible for the separation.

Thus, in condensed phase, to carry out the separation the void space must be filed with an adequate amount of desorbent, also in which is the liquid phase.

This, besides the increase of the costs for the subsequent separation of the desorbent, always present in a great excess, does not permit the loading capacity of the solid to be thoroughly exploited, the desorbent being competitive in the absorption.

The operation in vapor phase is thus the third feature which distinguishes this invention and turns into an undeniable advantage if it is considered that the volume of the zeolitic crystalline cavities is about 15% of the total void volume.

In the remaining void volume there remain, both in the adsorption and in the desorption phase, vapors with densities lower by 250 to 300 times those of like condensed phases.

On the other hand the adsorption in the intercrystalline zeolitic cavities takes place, under the selected operating conditions, without an appreciable loss of the loading capacity in comparison with a like process carried out in liquid phase. Another advantage is represented by the low resistance to the mass transfer in vapor phase, as it can be appreciated from the steepness of the break through curves. That permits the reactions of desorbent displacement by the xylenes being adsorbed and viceversa that of displacement of xylenes by the desorbent to readily take place.

In fact, under the adopted operating conditions, there are sufficient contact times with the adsorbent solid particles of between 5 and 90 seconds to obtain the separation of metaxylene with high concentration and high yields.

As the desorbent, toluene has been preferably used, it having an affinity towards the solid which is intermediate between those of metaxylene and ethylbenzene and is readily separable by distillation. It is possible, according to the opportunity, to operate in several manners.

If the interest is mainly in the separation of metaxylene the mixture of xylenes can be fed until the first fraction coming out is collected, comprising metaxylene and desorbent, and is stopped just before the break through of ethylbenzene. It is however also possible to collect, still in the adsorption phase, a second fraction consisting of metaxylene, plus ethylbenzene plus desorbent, if the operation is stopped just before the appearance of paraxylene. Such a situation is described in the example 3. It is possible to recover thereafter metaxylene from this second fraction, after the desorbent has been distilled and recycled, by passing the mixture of metaxylene and ethylbenzene onto an adsorption bed having identical characteristics and under the same conditions used for the preceeding separation. In the example 2 there is reported, for this purpose, an example of separation of the binary mixture metaxylene/ethylbenzene.

Whatever the operating procedure used, in the desorption phase a fraction, which is the last, containing paraxylene plus desorbent is always recovered. It is however possible, during the desorption, to recover also a fraction containing ethylbenzene plus paraxylene which, upon distillation of the desorbent, can be subjected to further refining always according to the same operating conditions and with the same type of adsorbent. If an amount of xylenes, is fed which is about equal to the loading capacity of the column or slightly greater, under the proposed operating conditions, in the desorption phase a fraction will exist, containing all three xylenes, which shall have to be recycled. If such a recycle is to be avoided and it is desired to exactly collect the above described four fractions, a lower amount of xylenes, corresponding to about one half of the amount needed for the bed saturation, must be fed. In the example 4 such a situation is illustrated.

The recovery of other purified products does obviously reduce the cost of the whole operation. The separation of metaxylene from the other isomers can be made continuous by operating with an adequate number of columns suitably staggered so as to close the full cycle comprising the adsorption and desorption phases. Each column, inserted in the cycle, operates in the same way, whereby it is enough to describe the operation of a single column. Such a operating manner, although discontinuous with reference to the single column, is the most convenient for the simplicity of the operations and because the adsorption bed is fully utilized as regards the separation function, by operating in vapor phase. The volumes of xylenes and of the desorbent, fed at the several phases, in fact, are exactly those that the intercrystalline zeolitic cavities are able to receive.

(a) Adsorption phase

In a column already saturated with toluene, and thus containing about 0.13 to 0.17 g of toluene per gram of zeolite, corresponding to the loading capacity of the adsorption bed, a mixture of metaxylene, ethylbenzene and paraxylene, is fed, after evaporation, at a temperature of between 145° and 250° C. preferably between 150° and 200° C. The amount of mixture to be fed depends on the number and type of fractions which one desires to collect.

If the prevailing interest is that of recovering the metaxylene it is advisable to feed an amount by volume of liquid, as measured at 25° C., corresponding to the amount of toluene already present in the column (0.15 to 0.20 cu.cm/g), apart from the possible amount by volume needed to push out of the column the separated metaxylene and other eventual fractions. The latter function however can also be fulfilled by the desorbent; in such a case, the amount of xylene mixture to be fed is exactly that which the intercrystalline zeolitic cavities are able to receive or less.

In the first case two fractions are recovered, the first consisting of metaxylene plus desorbent, the second of metaxylene plus ethylbenzene plus desorbent, as it can be appreciated in the example 3.

Of course the feeding of the xylene mixture is stopped just before the break through of paraxylene. The metaxylene can be then recovered also from the second fraction with a like process, under the same operating conditions and with the same adsorbent, upon the desorbent which is distilled, as it clearly appears from example 2.

If amounts of xylenes lower than those needed for the bed saturation and for obtaining the break through are fed, no fractions are obviously collected in the adsorption phase.

These fractions are all collected in the subsequent desorption phase. In the adsorption phase satisfactory separation of metaxylene is obtained at spatial velocities of the vapor of between 30 and 600 $h^{-1}$, with preference for the range of 100–350 $h^{-1}$.

(b) Desorption phase

The desorption is an extended washing of the bed with a desorbent previously evaporated, under the same conditions of pressure and temperature described as regards the adsorption. As desorbent the toluene is preferably used since it has an affinity for the solid intermediate between those of metaxylene and ethylbenzene thus promoting the desired separation.

Depending on the operating conditions followed in the preceeding adsorption phase the number and the type of fractions which can be collected in the desorption will vary. Two cases can be foreseen; in the first one of the amount of xylenes fed is such as to allow for the collections of two fractions during the adsorption as already seen. In this case during the desorption three fractions can be collected, the first one consisting of a mixture of the unseparated xylenes together with the desorbent, the second consisting of ethylbenzene, paraxylene and desorbent, the third of paraxylene and desorbent. In the second case the amount of xylenes is less than that needed to achieve the break through. All the fractions are then collected in the desorption phase. With amounts of xylenes equal or nearly equal to those necessary for the adsorbent saturation, the fractions which can be collected are always five and are always the same.

The amount of xylenes to be fed to the column can be however adjusted so that the meta/para separation is complete; in such a case the fractions become four, since the intermediate one, in which the three components were not separated and formed a recycle does disappear.

Such a situation is described in the example 4.

The fractions consisting of binary mixtures plus the desorbent can be separated always in the same way, upon the desorbent, is distilled.

The flow rate being the same, the desorption is a process slower than adsorption, whereby it is often convenient to operate with toluene flow rates higher than the preceding phase.

The time needed for the completion of the desorption, in fact, is generally inversely proportional to the flow rate of toluene (example 5). This can be adjusted, therefore, so as to obtain equal times for the two phases or, in the case in which a continuous equipment is used, so as to complete a cycle with a predetermined number of columns. The possibility of widely varying the flow rate of desorbent with respect to the flow rate of xylenes being adsorbed, without an appreciable effect on the separation between the several components, allows for remarkable flexibility of the system.

The most convenient spatial velocities remain between 30 and 600 $h^{-1}$ like the corresponding adsorption phase.

As confirmed by the following examples, contrary to what was foreseeable, it has been found in a completely unexpected manner that the separation of the xylenes in the vapor phase is not only industrially possible and feasible, but also that it takes place in a much more convenient way with respect to the case in which the operation, under the same operating conditions, is carried out in a condensed phase.

Without intending to predetermine undue limitations upon the present invention, it seems plausible that the advantages of the process of the invention can be attributed to the reasons as hereinafter listed:

(1) The loading capacity of the zeolite, meant as the maximum amount of xylenes which can be accepted within the intercrystalline zeolitic cavities remains practically unchanged with respect to the operation in the liquid phase.

(2) The amounts of products which are fed, in the vapor phase, on the adsorbing bed can be easily adjusted so as to be comparable with the loading capacity of the adsorbent, permitting a greater flexibility of the separation operation.

(3) The void spaces of the column are filled with vapors having densities 200 to 300 times less than those of like condensed phases. That permits one to obtain for the separated products, much higher concentrations and consequently the use of lower amounts of desorbent.

(4) By operating in the vapor phase, there occur in a very remarkable manner some behaviour characteristics, which are positive for the purposes of the separation, which can be found in displacement chromatography. In fact, the several components of the mixtures to be separated come out of the column with characteristic times depending on the respective distribution coefficients, as pushed by the desorbent which as regards the components having low distribution coefficient acts as a piston. The consequence is that the metaxylene, having the loxest distribution coefficient, is first pushed out of the column at a very high concentration, near to 100%, since the impurity is the desorbent.

Consequently, there takes place for the metaxylene an enrichment, with respect to the feeding concentration, in the fraction coming out first from the adsorbing bed. In a minor extent the same occurs also for the ethylbenzene. The just described behaviour can be clearly seen in the break through curves reported in the FIGS. 1, 2 and 3.

(5) From the preceeding considerations it is understood that, by operating in the vapor phase, all the adsorbent is used in carrying out the separation, i.e. the separating capacity of the adsorbing material is completely expoited although the operation takes place discontinuously.

Thus, there is no need of complicated operations in order to optimize the utilization of the bed as in the liquid case and the amount of zeolite to be used for a like separation process in the liquid phase is lower.

In the following examples reference is made to several break through curves, as experimentally obtained by using for the analysis the effluent vapors from the adsorption column and two gas-chromatographs in line, provided with automatic sampling valves, maintained at the temperature of the column.

EXAMPLE 1

Separation of metaxylene from a binary mixture (1:1 in moles) with paraxylene, until the equilibrium is attained (break through curves).

In a stainless steel column, having 1.1 cm diameter and 36 cm length, 23 g of a zeolite exchanged with potassium and previously treated as above described were charged.

A 50% by mole mixture of the two isomers, metaxylene and paraxylene, was fed, after evaporation, at atmospherical pressure to the bed, maintained at 160° C., with a flow rate of 0.09 cu.cm/min., as measured in the liquid at 25° C.

There are obtained two break through curves, respectively relating to metaxylene and to paraxylene, as reported in FIG. 1. From these break through curves it is possible to determine the adsorbed amounts of metaxylene and paraxylene which are $3.56 \times 10^{-4}$ moles/g and $1.23 \times 10^{-3}$ moles/g respectively.

The amount of separated metaxylene is 61% with respect to that fed at the same time.

The paraxylene/metaxylene selectivity which can be deduced from this experiment was reported in the preceeding Table 1. As it can be seen, the concentration of metaxylene attains values near to 100%, the residue being toluene.

EXAMPLE 2

Separation of metaxylene from a binary mixture 1:1 with ethylbenzene until the equilibrium is attained (break through curves).

A copper column is employed, having 1 cm diameter and 1 m length, containing 50 g of zeolite Y of the already described type. The mixture, 50% by mole of ethylbenzene and metaxylene was fed at atmospherical pressure and at 150° C. with a flow rate of 0.2 cu.cm./min.; (liquid volume measured at 25° C.).

The break through curves as obtained are reported in FIG. 2. From these curves it can be deduced that the adsorbed amounts of methaxylene and ethylbenzene are $5.15 \times 10^{-4}$ moles/g and $9.73 \times 10^{-4}$ moles/g respectively.

The amount of separated metaxylene is in this case 40% of that fed at the same time. The selectivity is reported in Table 1.

In this case also the molar fractions of the effluent metaxylene increase to values near to unity the residue being toluene.

EXAMPLE 3

Separation of metaxylene from ternary mixtures 1:1:1 with ethylbenzene and paraxylene, until the equilibrium is attained (break through curves).

This experiment was carried out in the same copper column, having 1 cm diameter and 1 m length containing 50 g of zeolite.

This column was fed with a mixture (1:1:1 by moles) of metaxylene, ethylbenzene and paraxylene at atmospherical pressure, at 150° C., with a flow rate of 0.29 cu.cm/min., measured as liquid volume at 25° C.

The break through curves as obtained for the three components are reported in FIG. 3. From these curves it is seen that the amount of recovered metaxylene corresponds to 28% of that fed at the same time.

The composition of this fraction and of the subsequent one, rich in ethylbenzene is reported in Table 2.

As it can be seen, by operating with three components there occurs an enrichment of the concentration also for the ethylbenzene besides that for the metaxylene.

TABLE 2

|  | m-xylene (g) | ethylbenzene (g) | desorbent (g) |
|---|---|---|---|
| 1st fraction | 0.86 | — | 2.15 |
| 2nd fraction | 0.77 | 0.10 | 0.01 |

EXAMPLE 4

Separation of the several fractions obtainable in the desorption from a ternary mixture (1:1:1 on moles) of metaxylene, ethylbenzene and paraxylene.

A first experiment was carried out in the same column of the preceeding example and under the same operating conditions as regards temperature and pressure, 9.0 cu.cm. of a mixture (1:1:1 by moles) of metaxylene, paraxylene and ethylbenzene being fed at 0.31 cu.cm/min so as to saturate the adsorbing bed.

Figure 4:
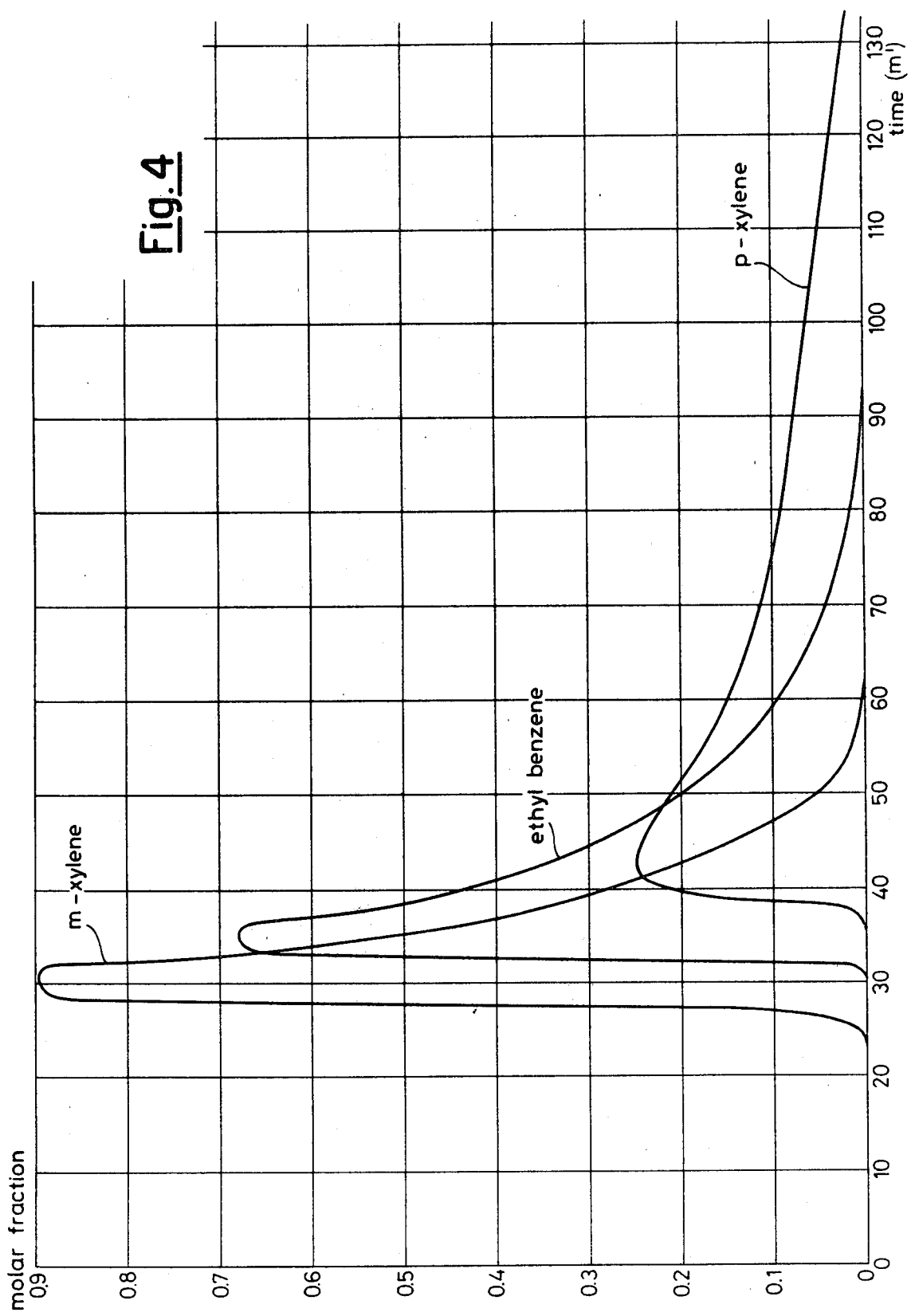

Then the feeding of xylene mixture is stopped and the desorption with toluene at the same flow rate is started by collecting five fractions, which come out in the order viewable in FIG. 4 and with the composition given in the Table 3.

Figure 5:
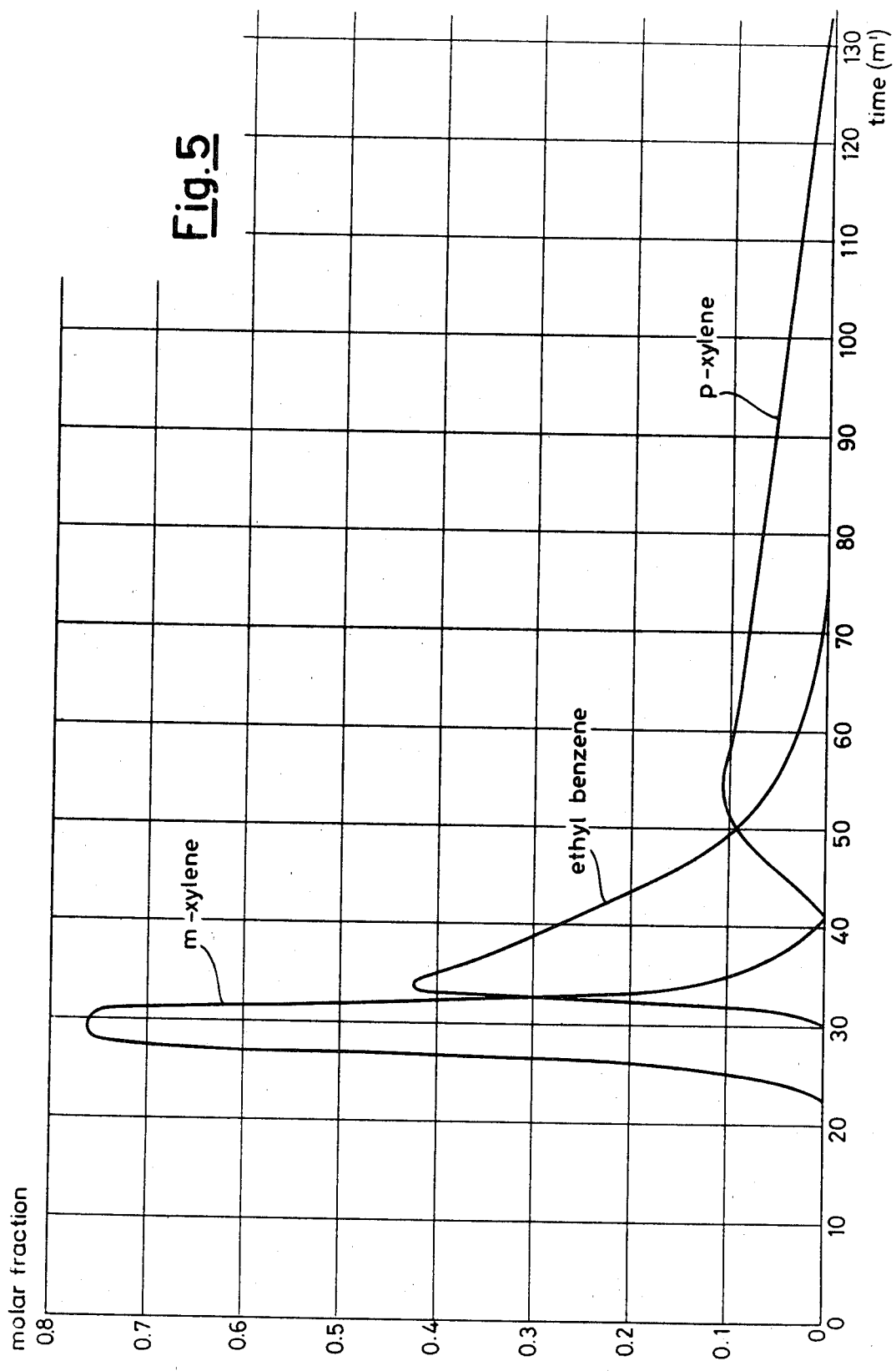

If a lower amount of xylenes is fed it is possible, by suitably adjusting such an amount, to completely separate the meta from paraxylene. There is in this case the possibility of collecting four fractions avoiding the intermediate fraction containing the non separated xylenes and which must be recycled. It is enough to feed an amount of 5 cu.cm., under the same conditions of temperature and pressure of the previously described experiment, with the same flow rate, to obtain the just described effect, viewable in FIG. 5. The composition of the four fractions is reported in Table 4.

TABLE 3

|  | mxylene (g) | ethyl benzene (g) | pxylene (g) | desorbent (g) | (g) |
|---|---|---|---|---|---|
| Fraction 1 | 0.81 | — | — | 1.07 | |
| Fraction 2 | 0.85 | 0.60 | — | 0.02 | |
| Fraction 3 | 0.83 | 1.82 | 1.20 | 3.31 | |
| Fraction 4 | 66 | 66 | 0.51 | 13.4 | |
| Fraction 5 | — | — | 0.51 | 13.4 | |

TABLE 4

|  | m-xylene (g) | ethyl benzene (g) | p-xylene (g) | desorbent (g) |
|---|---|---|---|---|
| Fraction 1 | 0.68 | — | — | 1.33 |
| Fraction 2 | 0.68 | 0.82 | — | 1.53 |
| Fraction 3 | — | 0.59 | 0.73 | 7.57 |
| Fraction 4 | — | — | 0.65 | 15.80 |

EXAMPLE 5

Effect of the flow rate on the adsorption or desorption rate. As previously mentioned, if amounts of xylenes lower than those necessary to fill the intercrystalline zeolitic cavities and to collect the separated metaxylene are fed, it is possible not only to carry out a better separation, but an easy method is available in order to forecast the performance of an adsorbing bed in the several operating conditions.

To this end, 2.2 cu.cm. of a binary mixture (1:1 by moles) of metaxylene and paraxylene were fed to the adsorbing bed already described in the example 1, at the temperature of 190° C. and under atmospherical pressure, with varying flow rates both in the xylene feeding phase and in the desorption phase. The flow rates used were 0.145, cu.cm/min., 0.4 cu.cm/min. and 0.5 cu.cm./min. As it can be seen from the plot of FIG. 6 the separation was not, as a matter of fact, influenced by the increase of flow rate. This means that the whole event is relevantly accelerated by being only related to the volume of eluant. That is true also for higher flow rates. Like behaviour takes place, at 150° C., and for ternary mixtures. It is thus possible vary the flow rate both in the adsorption phase and in the desorption phase the involved phases being consequently accelerated. It is anyhow advisable to remain within the already indicated limits of spatial velocity of between 30 and 600 $h^{-1}$, with preference for the 100–350 $h^{-1}$ range. In the preceding specification under the generic name "xylenes" ethylbenzene was also contemplated as being an aromatic hydrocarbon with 8 carbon atoms, an isomer of those more properly called xylenes.

We claim:

1. A process for separating metaxylene from a mixture of aromatic $C_8$ hydrocarbons consisting of ortho-, meta and para-xylene and ethylbenzene, said process comprising
   (1) initially saturating a zeolite Y adsorption bed with vapors of a desorbent, then,
   (2) passing said mixture in the vapor phase through a potassium-exchanged adsorption bed of said zeolite Y at a spacial velocity of between 30 and 600 $h^{-1}$ and at a pressure between atmospheric and 2 atmospheres to displace said desorbent, the adsorption bed being maintained at a temperature of between about 145° C. and 250° C., thereby saturating the adsorption bed with the mixture of aromatic $C_8$ hydrocarbons,
   (3) collecting and removing from the saturated adsorption bed, in a desorption phase, (i) a first fraction of metaxylene plus desorbent, and (ii) a second fraction of a mixture of metaxylene, desorbent and an aromatic $C_8$ hydrocarbon isomer present in the starting mixture and having an affinity for the adsorbent bed second only to the affinity of that of metaxylene, and
   (4) recycling the first fraction (i) of metaxylene plus desorbent collected in step (3) to the adsorption bed in step (2).

2. A process for separating metaxylene from a mixture consisting essentially of ortho-, para- and metaxylene, said process comprising the sequential steps of:
   (1) saturating a potassium-exchanged zeolite Y adsorbent bed with vapors of a desorbent, then
   (2) passing the xylene mixture in the vapor phase through the thus-treated zeolite Y adsorption bed at a spacial velocity of between 30 and 600 $h^{-1}$ and at a pressure between atmospheric and 2 atmospheres to displace said desorbent, the adsorption bed being maintained at a temperature of between about 145° C., and about 250° C., whereby the amount of xylene vapors supplied to said adsorbent bed is about one-half the amount required to saturate same, and thereafter
   (3) recovering, in a desorption phase, a (i) first fraction consisting of one of said xylenes plus desorbent, (ii) a second fraction consisting of a binary mixture of two of said xylenes plus desorbent, (iii) a third fraction consisting of a binary mixture of two of said xylenes plus desorbent, and (iv) a fourth fraction consisting of one of said xylenes plus desorbent.

3. The process according to claim 1 or 2, wherein the adsorption is conducted at a temperature of between 150° C. and 200° C.

4. The process according to claim 1 or 2, wherein the adsorption pressure is atmospheric.

5. The process according to claim 1 or 2, wherein said desorbent is toluene.

6. The process according to claim 1 or 2, wherein said spacial velocity is between 100 and 350 $h^{-1}$.

7. The process according to claim 1 or 2, wherein the desorption is conducted at a temperature of between about 150° C. and about 200° C. at atmospheric pressure using toluene as the desorbent.

8. The process according to claim 1, wherein the aromatic $C_8$ hydrocarbon mixture supplied in step (2) is an amount corresponding to the sum of (i) the loading capacity of the adsorption bed, plus (ii) the volume required to push at least the first fraction of purified metaxylene plus desorbent from said adsorption bed.

9. The process according to claim 1, wherein the second fraction (ii) collected in step (3) consists of metaxylene, ethylbenzene and desorbent.

10. The process according to claim 1, wherein the flow rate in the desorption phase is greater than the amount necessary to saturate the adsorption bed.

11. The process according to claim 1 or 2, wherein the loading capacity of said zeolite is from about 0.13 to about 0.17 grams of the adsorbed mixture of xylenes plus ethylbenzene per gram of said zeolite.

* * * * *